United States Patent [19]

Baratta et al.

[11] Patent Number: Plant 5,435

[45] Date of Patent: Apr. 9, 1985

[54] CARNATION NAMED LONTARION

[75] Inventors: Nicoletta Baratta; Giacomo Nobbio, both of San Remo, Italy

[73] Assignee: Laboratoire de Physiologie Vegetale de La Londe, Antibes, France

[21] Appl. No.: 522,100

[22] Filed: Aug. 11, 1983

[51] Int. Cl.[3] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new carnation cultivar particularly distinguished by its bright red flowers of medium size having many very frilled petals which lend a very distinctive character to the ball shape of the bloom which is carried on strong, rigid stems which provide particular advantage when the blooms are employed for decorative uses either alone or in arrangements with other flowers in vases. This plant has a very vigorous and upright growth habit reaching a height of about 110 cm. providing very strong flower stems when cut at the tenth node.

1 Drawing Figure

BACKGROUND OF THE NEW PLANT

Our new carnation cultivar originated as a seedling produced by our crossing of selected identified plants maintained in our breeding stock in nursery at San Remo, Italy. This particular seedling was selected by us for propagation and test because of its apparently vigorous growth habit and profuse production of very beautiful, bright red, ball shaped flowers, the very frilled petals of which provide an especially attractive appearance. We propagated this new plant through several generations, by means of cuttings, at San Remo, Italy, and thereby determined that the novel and distinctive characteristics of the parent plant were retained from generation to generation and appeared to be firmly fixed. This new plant is now being propagated in nurseries at La Londe, Les Maures, Var, France, in vitro and by cuttings.

DESCRIPTION OF THE DRAWING

Our new variety of carnation plant is illustrated by the accompanying photographic drawing which shows, in full color, an arrangement of buds, partially opened flowers and full blooms, the colors shown being as nearly true as it is reasonably possible to be had by conventional photographic procedures.

DESCRIPTION OF THE NEW PLANT

The following is a detailed description of our new carnation plant based upon observations of greenhouse grown plants made at La Londe, France, in the Spring of 1983, the color designations being according to The R.H.S. Colour Chart of The Royal Horticultural Society at London, England.

THE PLANT

Origin: Seedling.

Parentage:

*Seed parent.*—Stock Item No. 8 762 (unpatented).

*Pollen parent.*—Stock Item No. 8 391 (unpatented).

Classification:

*Botanic.*—Hybrid *Dianthus caryophyllus.*

*Commercial.*—Standard carnation.

Form: Tall, leafy bush.

Height: At eight months, averaging 110 cm.

Main stem: Length is less than 15 cm. due to pinching.

Branching character: Good, with at least four stems emitted near the ground.

Growth: Vigorous, upright and with excellent strength.

Foliage:

*Quantity.*—Rather abundant.

*Number of leaves.*—More than 120.

*Size of leaf.*—At 7th node, about 14.5 cm. in length and about 7.5 mm. in width.

*Shape of leaf.*—Linear with curved margins and acuminate tip.

*Texture.*—Leathery.

*Color.*—Upper side — 189A. Under side — 189A.

*Ribs, veins and rachis.*—Hardly noticeable.

THE BUD

Form: Ovoid.

Size: Medium.

*Diameter.*— About 2.2 cm.

*Length.*—About 3 cm.

Color of petals: When sepals first divide and when petals begin to unfurl, the color is the same as at full bloom.

Sepals:

*Shape.*—Generally ovate in the upper part, joined at lower part, and having a sharply pointed tip.

*Number.*—Five.

*Character.*—Hooded over the bud and when flowers open, the sepals stand up.

*Color.*—Inside — Greenish White. Outside — 138A and 144C.

*Striae.*—Longitudinal.

Calyx:

*Form.*—Bell shaped.

*Size.*—Medium.

*Aspect.*—Smooth.

*Splitting.*—Calyx splits very rarely.

Flower stem:

*Character.*—Erect and rather rigid.

*Color.*—189A.

THE FLOWER

Blooming habit: Profusely and recurrent in midseason of Spring and Fall.

Size of bloom: Medium.

*Diameter.*—Average 8.2 cm.

*Depth.*—Average about 5.7 cm.

Borne: Singly.

Form: When bloom first opens, high centered. When bloom matures, ball shaped.

Petalage:

Number of petals.—Averaging about 66.

*Arrangement.*—Imbricated

*Form.*—Fan shaped with rounded angle with deeply serrated outer end margins.

*Texture.*—Soft

*Appearance.*—Satiny

*Color.*—Outer petals: Body — 45B and 45C. Base — Yellowish Green. Reverse side — 45C. Inside petals: Body — 45B and 45C. Base — Yellowish Green. Reverse side —45C.

Petaloids: From 2 to 8 in number.

*Size.*—Smaller than the petals.

*Color.*—The same as petals.

*Flower stem:*

*Length.*—About 75 cm. when cut at tenth node.

*Character.*—Upright with good strength.

*Color.*—189A.

Fragrance: Absent or very light.

Persistence: Petals hang on and wither.

Disease resistance: Rather resistant to *Fusarium oxysporum* as observed at Antibes, Alpes-Maritimes, France.

Lasting quality: As cut flower — In vase keeping, at least ten days.

REPRODUCTIVE ORGANS

Stamens:

*Number.*—4 To 11.

*Arrangement.*—Around the pistils.

*Anthers.*—Size: Less than 4 mm. Color: Whitish.

*Filaments.*—Color — Whitish.

Pistils: From 2 to 4.

*Styles.*—Color — Light Red.

*Stigmas.*—Color — Light Red.

Character of ovaries:

*Color.*—Greenish Yellow.

Compared to "Scania", which our new variety most nearly resembles, the new variety is distinguished by having more frilled flowers and longer internodes, as well as being rather tolerant to *Fusarium oxysporum*. Other differences are not so determined as they may vary according to culture and environmental conditions.

We claim:

1. The new and distinct carnation cultivar, substantially as herein shown and described, characterized by its abundant production of bright, medium sized blooms, its regularly recurrent blooming habit, and its resistance to *Fusarium oxysporum*.

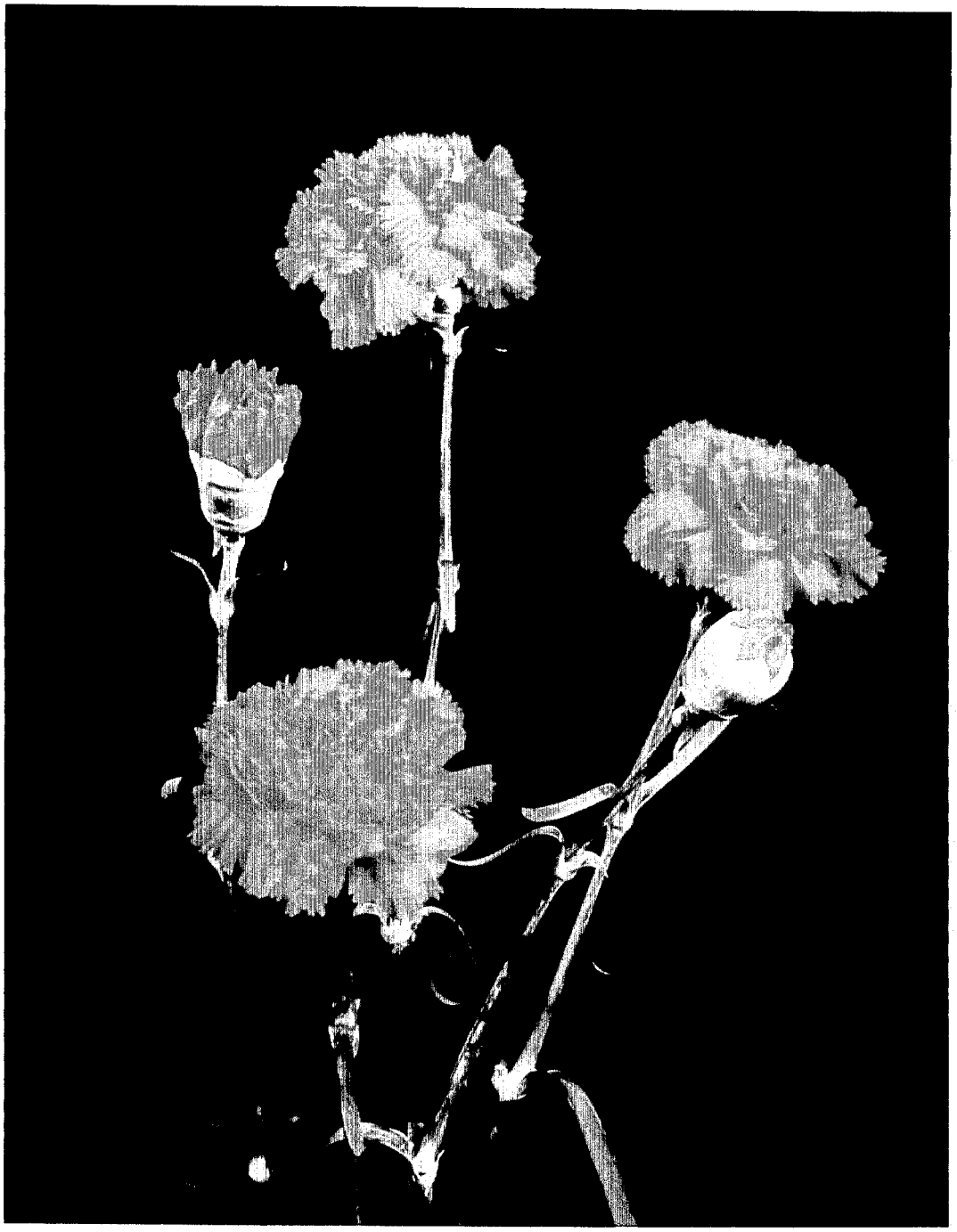

* * * * *